(12) United States Patent
Lee

(10) Patent No.: US 8,156,940 B2
(45) Date of Patent: Apr. 17, 2012

(54) DEVICE FOR SNORING PREVENTION

(76) Inventor: Seung-Kyu Lee, Seoul (KR)

( * ) Notice: Subject to any disclaimer, the term of this patent is extended or adjusted under 35 U.S.C. 154(b) by 93 days.

(21) Appl. No.: 12/513,366

(22) PCT Filed: Nov. 16, 2007

(86) PCT No.: PCT/KR2007/005784
§ 371 (c)(1),
(2), (4) Date: May 4, 2009

(87) PCT Pub. No.: WO2008/060122
PCT Pub. Date: May 22, 2008

(65) Prior Publication Data
US 2010/0065067 A1 Mar. 18, 2010

(30) Foreign Application Priority Data
Nov. 17, 2006 (KR) .................... 10-2006-0113891

(51) Int. Cl.
*A61F 5/56* (2006.01)
*A61C 3/00* (2006.01)
(52) U.S. Cl. ............................. 128/848; 433/6
(58) Field of Classification Search .................. 128/848, 128/846, 859, 860, 861; 433/6
See application file for complete search history.

(56) References Cited

U.S. PATENT DOCUMENTS

| | | | |
|---|---|---|---|
| 5,427,117 A | 6/1995 | Thornton | |
| 5,868,138 A | 2/1999 | Halstrom | |
| 5,884,628 A | 3/1999 | Hilsen | |
| 5,941,247 A | 8/1999 | Keane | |
| 6,055,986 A * | 5/2000 | Meade | 128/848 |
| 6,675,802 B1 | 1/2004 | Thornton | |
| 6,845,774 B2 | 1/2005 | Gaskell | |
| 2002/0000230 A1* | 1/2002 | Gaskell | 128/848 |
| 2005/0199247 A1 | 9/2005 | Garabadian | |
| 2009/0090371 A1* | 4/2009 | Toussaint | 128/848 |

FOREIGN PATENT DOCUMENTS

| | | |
|---|---|---|
| JP | 2002-519137 A | 7/2002 |
| JP | 2005-312853 A | 11/2005 |
| KR | 2006-0089860 | 8/2006 |
| KR | 2007-0018643 | 2/2007 |
| WO | WO 94/23673 | 10/1994 |
| WO | 00/01317 A1 | 1/2000 |

\* cited by examiner

*Primary Examiner* — Patricia Bianco
*Assistant Examiner* — Tarla Patel
(74) *Attorney, Agent, or Firm* — Ladas & Parry LLP

(57) ABSTRACT

Provided is a snoring prevention device including an upper support supported by upper teeth of a patient, an upper protruding part provided at the upper support to protrude downward from the upper support, a lower support supported by lower teeth of the patient, and a lower protruding part provided at the lower support to protrude upward from the lower support and caught to a front side of the upper protruding part.

14 Claims, 8 Drawing Sheets

DEVICE FOR SNORING PREVENTION

TECHNICAL FIELD

The present invention relates to a device for preventing snoring, and more particularly, to a device for preventing snoring during sleep to enable a deep sleep.

BACKGROUND ART

In general, snoring occurs when air is not able to easily pass through the throat due to narrowing of the throat before the air enters in the throat when a person breathes. Thus, snoring is a symptom indicating a breath difficulty during sleep. When one breathes, air passes through soft human body parts such as the palate, the uvula, the tonsils, and the tongue. During the day, surrounding muscles help these body parts maintain the original positions so that the passage of air is not blocked and no sound is generated. However, during sleep, these muscles are relaxed and sag, thereby narrowing a part of the air passage. Thus, when the air passes through the narrowed air passage, soft tissues are vibrated to make snoring sounds.

In extreme cases, the air passage can be temporarily blocked due to severe muscle relaxation during sleep or high obesity. At this time, air does not pass toward the lungs at all. This condition is known as an obstructive sleep apnea syndrome.

When such a condition is prolonged, since fresh air is not supplied to the lungs, the brain detects the lack of air and thus orders the body to be awakened and the muscles to contract to reopen the air passage. Then, the patient can take one deep breath and resume breathing. If this phenomenon repeatedly occurs every night, the patient does not get much sleep, and as a result feels tired and very sleepy during the day. This may cause mishaps such as car accidents. Also, when the phenomenon continues for a long time, a burden to the heart or lungs increases such that severe side effects such as high blood pressure, arrhythmia, and myocardial infraction may occur.

To treat the sleep apnea syndrome, a nasal cavity operation or a pharynx removal laser operation may be performed, or a snoring prevention pillow or mouthpiece device may be used.

First, although a nasal cavity operation and a pharynx removal laser operation can temporarily reduce snoring, the symptom improved after the operation may be degraded after a period of time has elapsed.

The snoring prevention pillow has a merit in that it does not need an operation. However, the pillow does not work properly because it frequently deviates from its original position during sleep.

The mouthpiece device is designed to prevent snoring by pulling a lower jaw forward by inserting the device between the teeth. The device pulls the lower jaw forward so that a gap between the palate and the uvula, the tongue root, and the tonsils connected to the palate is increased to widen the air passage in the throat. The widened air passage enables the intake air for breathing during sleep to freely pass through the throat while avoiding the uvula, the tongue root, and the tonsils. Thus, vibrations of the palate and the tonsils due to the passage of air are completely prevented in advance.

The device has become widely used recently because an additional operation is unnecessary and the throat is maintained in a wide state during sleep. Korean Patent Publication No. 10-2006-0089860 discloses a device related to the above-described mouthpiece device.

A mouthpiece device 100 has a shape of a mouthpiece and has a teeth biting plate 101 on each of the upper and lower surfaces thereof, on which upper teeth 50 and lower teeth 60 can be disposed. When the upper and lower teeth 50 and 60 are disposed on the teeth biting plate 101, the lower jaw is naturally pulled forward so that the throat can be widened.

However, the conventional snoring prevention device 100 described above is required to be held in the patient's mouth with the upper and lower teeth fixed thereto for several hours during sleep, and thus is uncomfortable for the patient. In particular, patients having such a device held in their mouths with the uncomfortable pose find it difficult to sleep well and thus feel tired and sleepy the next morning.

DETAILED DESCRIPTION OF THE INVENTION

Technical Problem

Figure 1:
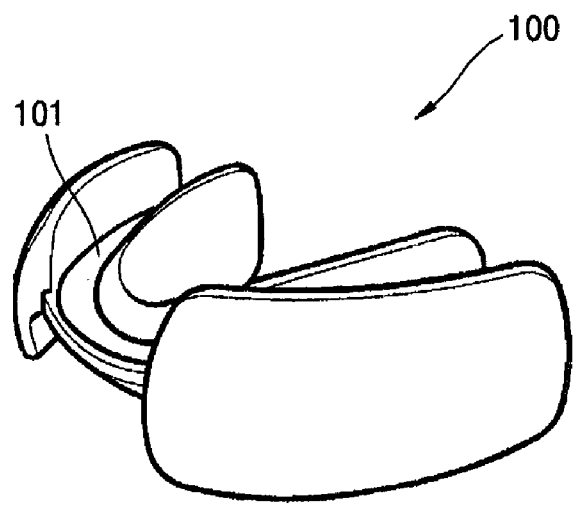
FIG. 1 is a perspective view of a conventional snoring prevention device.
Figure 2:
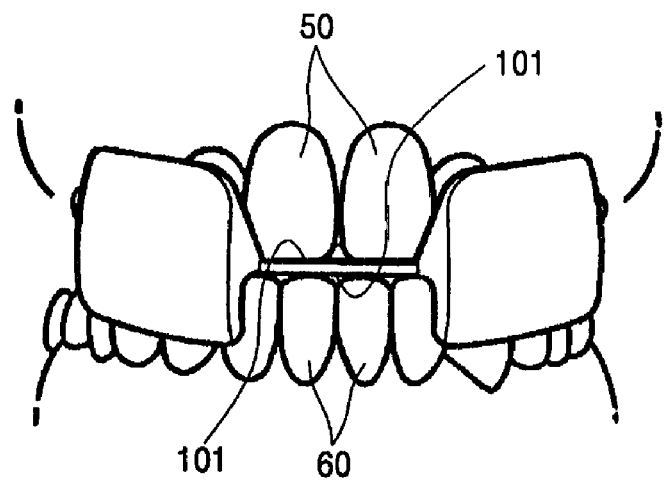
FIG. 2 illustrates the snoring prevention device of FIG. 1 inserted in a patient's mouth.

The present invention provides a snoring prevention device having a relatively simple structure, which can prevent snoring and allow the upper and lower teeth to move with respect to each other during sleep so as to aid natural sleep.

Technical Solution

According to an aspect of the present invention, there is provided a snoring prevention device comprising an upper support supported by upper teeth of a patient, an upper protruding part provided at the upper support to protrude downward from the upper support, a lower support supported by lower teeth of the patient, and a lower protruding part provided at the lower support to protrude upward from the lower support and caught by a front side of the upper protruding part.

The upper protruding part comprises a downward extension portion extending downwardly and a separation prevention portion extending from a lower end of the downward extension portion to protrude in a forward direction, and the lower protruding part comprises an upward extension portion extending upwardly and a separation prevention portion extending from an upper end of the upward extension portion to protrude downwardly and caught by an upper side of the separation prevention portion of the upper protruding part to prevent the upper support and the lower support from being separated from each other.

The device further comprises a first position adjustment unit to adjust the position of the upper protruding part with respect to the upper support in a forward/backward direction.

The first position adjustment unit comprises a plurality of screw holes arranged in the upper support to be separated from each other in the forward/backward direction and a screw member selectively coupled to one of the screw holes by penetrating the upper protruding part to allow the upper protruding part to be coupled to the upper support.

The device further comprises a second position adjustment unit to adjust the position of the lower protruding part with respect to the lower support in a forward/backward direction.

The second part position adjustment unit comprises a plurality of screw holes arranged in the lower support to be separated from each other in the forward/backward direction and a screw member selectively coupled to one of the screw holes by penetrating the lower protruding part to allow the lower protruding part to be coupled to lower support.

When the upper support is supported by the upper teeth and the lower support is supported by the lower teeth, the upper protruding part is located under front teeth of the upper teeth and the lower protruding part is located above front teeth of the lower teeth.

The upper protruding part and the lower protruding part is provided in a pair and, when the upper support is supported by the upper teeth and the lower support is supported by the lower teeth, a pair of the upper protruding parts and a pair of the lower protruding parts are symmetrically arranged between front teeth and molars at both sides.

A groove portion to accommodate at least one of the upper teeth is formed in the upper support and a groove portion to accommodate at least one of the lower teeth is formed in the lower support.

The groove portion of the upper support is formed to accommodate all upper teeth and the groove portion of the lower support is formed to accommodate all lower teeth.

Advantageous Effects

According to the snoring prevention device of the present invention having a simple structure, snoring can be prevented and jaw movement is allowed so that a patient can become easily accustomed to the device.

Best Mode

Hereinafter, embodiments of the present invention will be description in detail with reference to the accompanying drawings.

Figure 3:
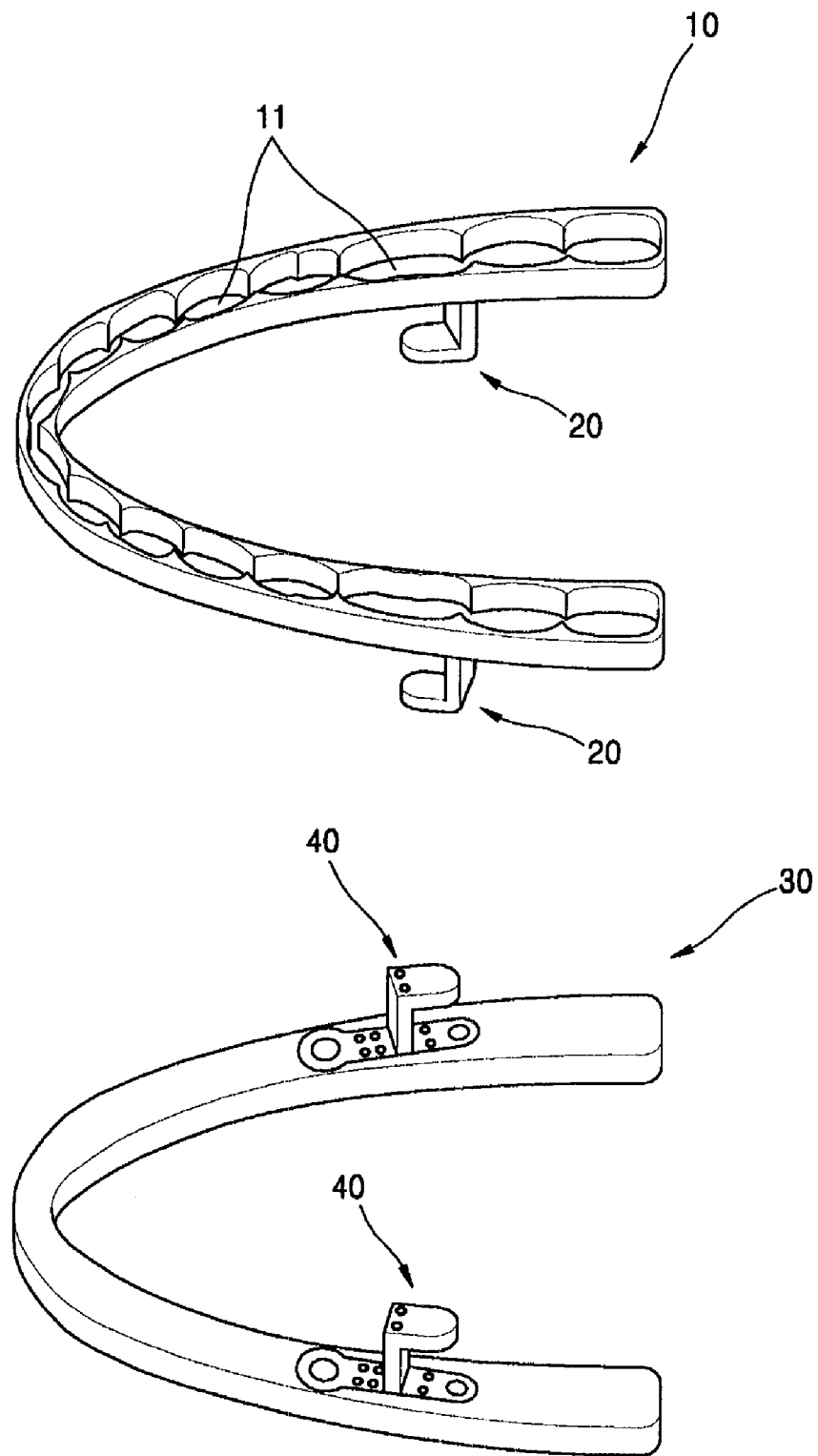
FIG. 3 is a perspective view of a snoring prevention device according to an embodiment of the present invention.
Figure 4:
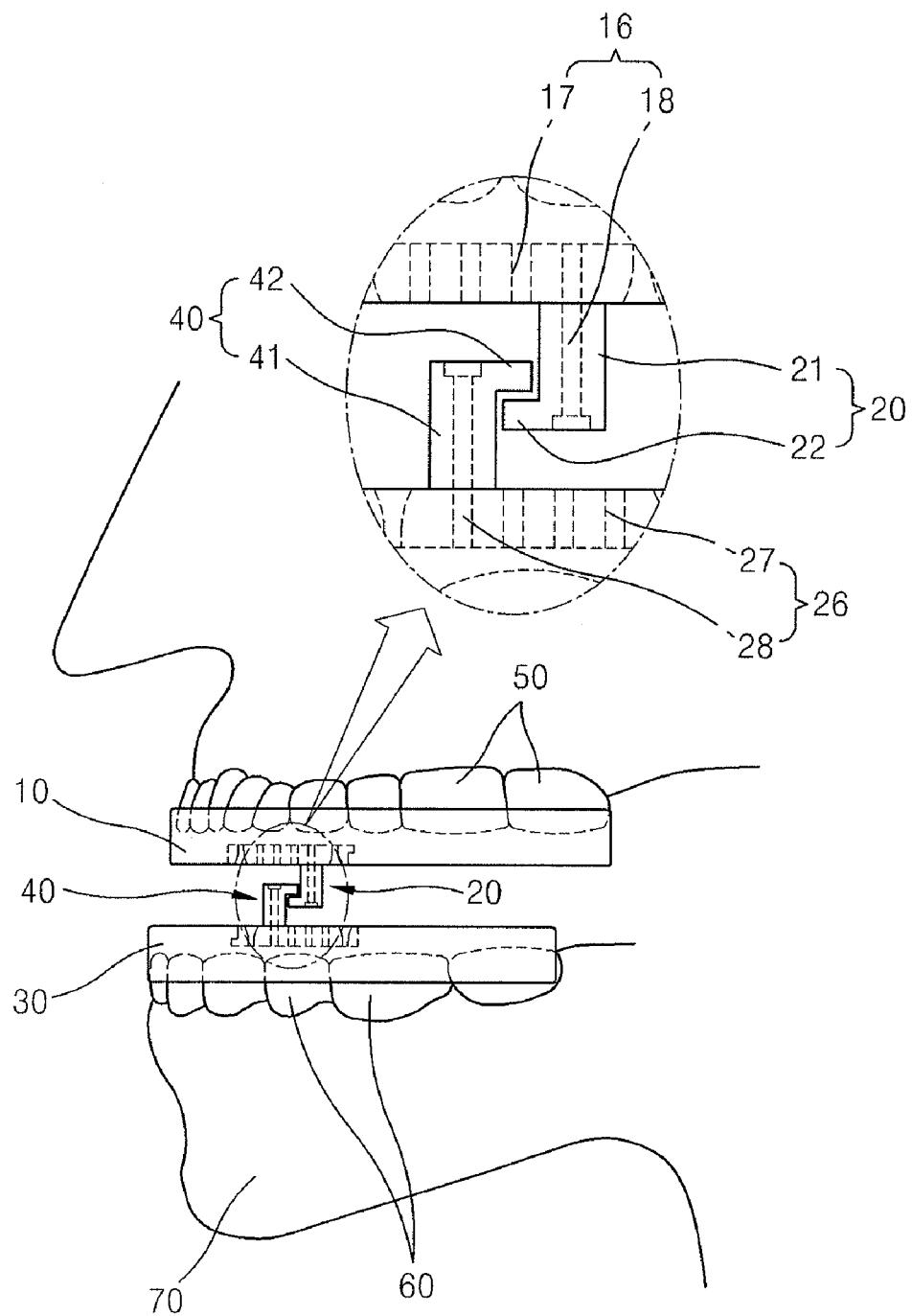
FIG. 4 illustrates the snoring prevention device of FIG. 3 inserted between the upper and lower teeth of a patient, according to an embodiment of the present invention.
Figure 5:
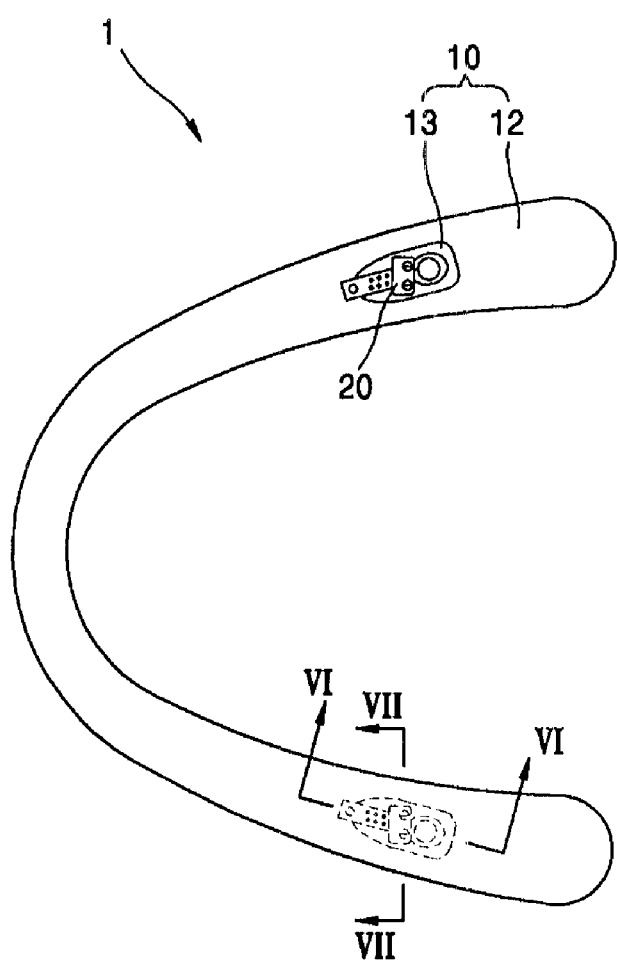
FIG. 5 is a plan view showing an upper support and an upper protruding part of the snoring prevention device of FIG. 3, according to an embodiment of the present invention.
Figure 6:
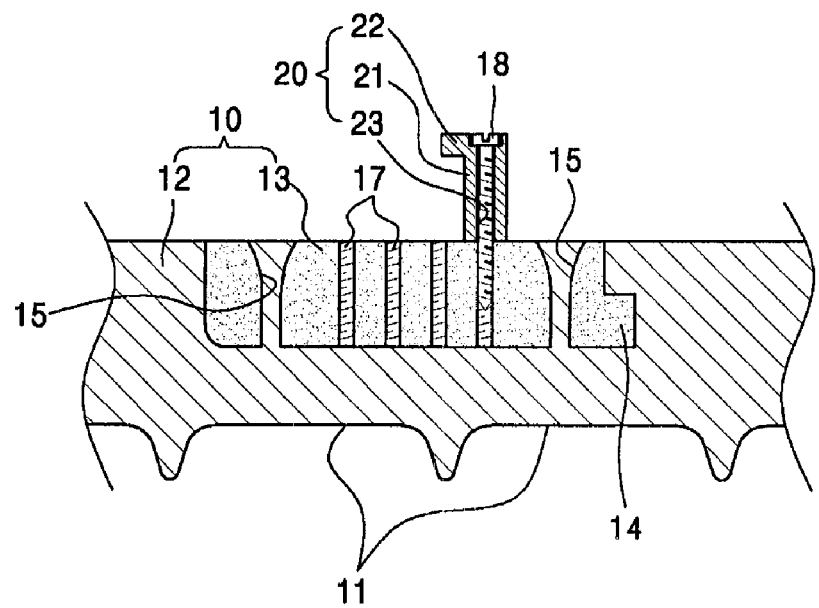
FIG. 6 is a cross-sectional view taken along the line VI-VI of FIG. 5, according to an embodiment of the present invention.
Figure 7:
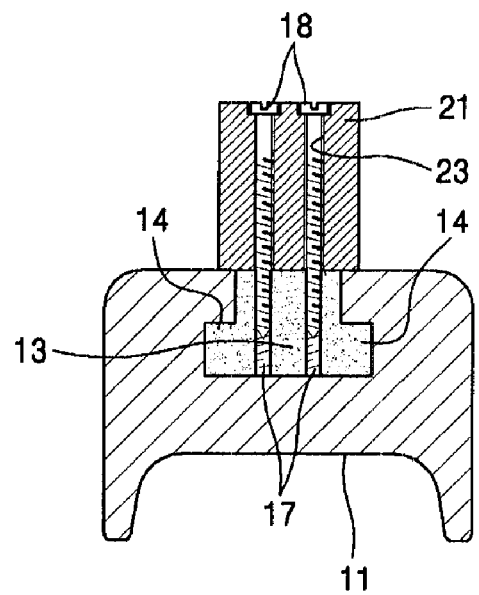
FIG. 7 is a cross-sectional view taken along the line VII-VII of FIG. 5, according to an embodiment of the present invention.

FIG. 3 is a perspective view of a snoring prevention device according to an embodiment of the present invention. FIG. 4 illustrates the snoring prevention device of FIG. 3 inserted between the upper and lower teeth of a patient, according to an embodiment of the present invention. FIG. 5 is a plan view showing an upper support and an upper protruding part of the snoring prevention device of FIG. 3, according to an embodiment of the present invention. FIG. 6 is a cross-sectional view taken along the line VI-VI of FIG. 5, according to an embodiment of the present invention. FIG. 7 is a cross-sectional view taken along the line VII-VII of FIG. 5, according to an embodiment of the present invention.

In the embodiments of the present invention, the word "forward" denotes a direction from the rear side to the front side of a human body; the word "backward" denotes a direction from the front side to the rear side of the human body; the word "upward" denotes a direction from the bottom side to the top side of the human body; and the word "downward" denotes a direction from the top side to the bottom side of the human body. In the present specification, the words "forward", "backward", "upward", and "downward" are defined as above unless defined otherwise.

A snoring prevention device 1 according to the present embodiment of the present invention includes an upper support 10, an upper protruding part 20, a lower support 30, and an upper protruding part 40.

The upper support 10 supports upper teeth 50 of a patient and has a groove portion 11 for inserting and accommodating the upper teeth 50. The groove portion 11 of the upper support 10 can accommodate all the upper teeth 50.

The upper support 10 includes a body portion 12 supported by the upper teeth 50 and a fixed portion 13 integrally formed in the body portion 12. The groove portion 11 is formed at one side of the body portion 12. The body portion 12 is formed of a synthetic material. The fixed portion 13 includes a fixed step 14, a fixed hole 15, and a screw hole 17.

The upper support 10 is manufactured by inserting the fixed portion 13 in a synthetic material such as acrylic resin in a liquid state and hardening the melted synthetic material. The hardened acrylic portion forms the body portion 12. The fixed portion 13 is formed at one side of the body portion 12 and the groove portion 11 having a shape corresponding to the upper teeth 50 of a patient is provided at the other side thereof. The fixed step 14 protrudes in a direction parallel to the lower surface of the upper teeth 50 from the outer surface of the lower portion of the fixed portion 13. As the body portion 12 covers the fixed step 14, the fixed portion 13 is prevented from becoming detached from the body portion 12. The fixed hole 15 penetrates the fixed portion 13 from the top to the bottom of the fixed portion 13. The diameter of the upper end of the fixed hole 15 is greater than that of the lower end of the fixed hole 15. When the body portion 12 of the upper support 10 is formed, the melted synthetic material is poured into the inside of the fixed hole 15 and hardened therein. The synthetic material hardened in the fixed hole 15 is coupled to the fixed portion 13 so that the fixed portion 13 is prevented from falling out of the body portion 12. In the present embodiment, the fixed portion 13 is prevented from becoming detached from the body portion 12 by using the fixed step 14 and the fixed hole 15.

A plurality of screw holes 17 are provided in a forward/backward direction of the upper support 10, and a detailed structure of the screw holes 17 will be described later.

The upper protruding part 20 is formed of a metal material at the upper support 10 to protrude downwardly with respect to the upper support 10. The upper protruding part 20 includes a downward extension portion 21 and a separation prevention portion 22. The downward extension portion 21 is a bar member extending downwardly. The upper portion of the downward extension portion 21 contacts the fixed portion 13 of the upper support 10 and the lower portion thereof is integrally formed with the separation prevention portion 22.

The separation prevention portion 22 is integrally formed with the the downward extension portion 21 and protrudes in a forward direction. A position adjustment hole 23 is provided in the upper protruding part 20 to penetrate the upper portion of the downward extension portion 21 toward the lower end of the separation prevention portion 22. The position adjustment hole 23 is provided in a pair and arranged in a direction approximately perpendicular to the direction in which the separation prevention portion 22 protrudes.

The lower support 30 and the lower protruding part 40 are described below. Since many of the constituent elements thereof correspond to those of the upper support 10 and the upper protruding part 20, the detailed descriptions and reference numerals for portions that do not need specific descriptions and drawing descriptions will be omitted.

The lower support 30 is supported by lower teeth 60 of the patient and has constituent elements corresponding to those of the upper support 10. The lower support 30 includes a body portion and a fixed portion corresponding to the body portion 12 and the fixed portion 13 of the upper support 10.

The lower protruding part 40 is installed at the lower support 30 to protrude upwardly with respect to the lower support 30. The rear side of the lower protruding part 40 is caught by the front side of the upper protruding part 20. Accordingly, the lower teeth 60 supported in the lower support 30 are maintained in a position forward of an original position where the lower teeth 60 are normally located.

In detail, when the lower teeth 60 are usually located slightly behind the upper teeth 50 in the forward/backward direction, when the snoring prevention device 1 is inserted in the patient's mouth as illustrated in FIG. 4, the lower teeth 60 can protrude beyond the upper teeth 50 in the forward direction. For a patient who does not need to move their lower teeth 60 in the forward direction, when the snoring prevention device 1 is inserted in the patient's mouth, it is sufficient to move the lower teeth 60 such that the upper teeth 50 and the lower teeth 60 face each other. Also, for a patient whose lower teeth 60 are normally positioned relatively far behind the upper teeth 50 in the forward/backward direction, when the snoring prevention device 1 is inserted in the patient's mouth, even if the lower teeth 60 are moved forward, the lower teeth 60 do not protrude beyond the upper teeth 50 in the forward/backward direction. For a patient whose lower teeth 60 protrude beyond the upper teeth 50 in the forward/backward direction, when the snoring prevention device 1 is inserted in the patient's mouth, the lower teeth 60 protrude further forward with respect to the upper teeth 50.

The lower protruding part 40 includes an upward extension portion 41 and a separation prevention portion 42. The upward extension portion 41 is a bar member extending upwardly.

The separation prevention portion 42 extends and protrudes backward from the top end of the upward extension portion 41. As the separation prevention portion 42 of the lower protruding part 40 is caught by the upper surface of the separation prevention portion 22 of the upper protruding part 20, an increase in the gap between the upper support 10 and the lower support 20 is prevented.

The lower protruding part 40 includes a position adjustment hole that penetrates the lower portion of the upward extension portion 41 to the top portion thereof. The position adjustment hole of the lower protruding part 40 corresponds to the position adjustment hole 23 of the upper protruding part 20.

In the present embodiment, the first position adjustment unit 16 that adjusts the position of the upper protruding part 20 in the forward and backward directions with respect to the upper support 10 is provided. And a second position adjustment unit corresponding to the first position adjustment unit is is provided at the lower protruding part 40. Since the second position adjustment unit has the same structure and function as the first position adjustment unit 16, the detailed description focuses on the first adjustment unit 16 be consistent in names of elements.

The first position adjustment unit 16 includes a plurality of the screw holes 17 and a screw member 18.

Although the screw holes 17 are described above in the description of the upper support 10, in detail, the screw holes 17 are arranged in the upper support 10 in the forward/backward direction and separated from each other. The screw holes 17 are arranged symmetrically in two rows in the left/right direction.

The screw member 18 penetrates the upper protruding part 20 and is selectively coupled to one of the screw holes 17 so that the upper protruding part 20 is installed at a desired position on the upper support 10. The screw member 18 penetrates the upper protruding part 20 and is screw coupled to the selected screw hole 17.

The second position adjustment unit 26 of the lower protruding part 40 includes a plurality of screw holes 27 and a screw member 28. The detailed structure of the lower protruding part 40 corresponds to that of the first position adjustment unit 16.

Each of the upper protruding part 20 and the lower protruding part 40 is provided in a pair. When the upper support 10 is supported by the upper teeth 50 and the lower support 30 is supported by the lower teeth 60, the pair of the upper protruding parts 20 and the pair of the lower protruding parts 40 are symmetrically arranged between the front teeth and molars at both sides.

The operation and effects of the snoring prevention device 1 according to the present embodiment as configured above are described below.

The upper support 10 and the lower support 30 are manufactured to fit to the shapes of the upper teeth 50 and the lower teeth 60 of a patient. The groove portion 11 of each of the upper support 10 and the lower support 30 is manufactured to accommodate all of the upper teeth 50 or the lower teeth 60. The manufactured upper support 10 and the lower support 30 are inserted around the upper teeth 50 or the lower teeth 60. The upper protruding part 20 and the lower protruding part 40 are respectively screw coupled to the upper support 10 and the lower support 30.

In detail, after the upper protruding part 20 is placed at a desired position of the upper support 10, the screw member 18 is screw coupled to the screw hole 17 of the upper support 10 by penetrating the position adjustment hole 23 of the upper protruding part 20. The upper protruding part 20 and the upper support 10 may be coupled using two screw members 18 so that the upper protruding part 20 is not rotated around the center axis of only one screw member 18. Also, the lower protruding part 40 and the lower support 30 are coupled in the same manner as the coupling of the upper protruding part 20 and the upper support 10.

When using the above snoring prevention device 1 according to the present embodiment of the present invention, the patient inserts the groove portion 11 of the upper support 10 around the upper teeth 50 and the groove portion 11 of the lower support 30 around the upper teeth 60 to support the snoring prevention device 1. A lower jaw bone 70 of the patient is pulled forward to allow the rear side of the lower protruding part 40 of the lower support 30 to be caught by the front side of the upper protruding part 20 of the upper support 10. As illustrated in FIG. 4, when the upper protruding part 20 and the lower protruding part 40 are coupled together, the upper protruding part 20 prevents the lower teeth 60 from moving backward. Also, the separation prevention portion 22 of the upper protruding part 20 prevents the gap between the upper support 10 and the lower support 30 from increasing. Accordingly, the gap between the upper teeth 50 and the lower teeth 60 is not widened.

In the present embodiment, the upper protruding part 20 restricts only the lower protruding part 40 from moving backward from the upper protruding part 20. The upper protruding part 20 is allowed to move in the left and right directions, that is, a direction perpendicular to a direction in which the separation prevention portion 22 of the upper or lower protruding part 20 or 40 protrudes. Thus, inconvenience felt by a patient wearing the snoring prevention device during sleep can be minimized.

In the meantime, according to the present embodiment, the inconvenience of manufacturing the snoring prevention device several times can be avoided. In detail, if a patient who first uses the snoring prevention device has lower teeth that are positioned relatively far behind the upper teeth in the forward/backward direction, the lower jaw bone needs to be slightly pulled forward step by step so that the patient can be accustomed to the snoring prevention device. In particular, in order to move the lower jaw bone to an optimal forward position, at least five jaw correction operations may be required.

To perform the jaw correction operations, the patient may need to visit a dental clinic over five times to alter the snoring prevention device for each step. In particular, snoring prevention device needs to be adjusted using silicon each time to change the accommodation position of the upper and lower teeth. This not only is expensive and labor-intensive but also requires the patient to visit the dental clinic each time to adjust the snoring prevention device according to the positions of the upper and lower teeth.

In contrast, according to the present embodiment, there is no need to manufacture an additional snoring prevention device for each step. The lower jaw bone can be pulled forward by merely changing the position of the upper or lower protruding part using the first or second position adjustment unit. That is, the upper support or the lower support is required to be manufactured only one time. To perform the correction job of gradually pulling the lower jaw bone forward, the screw member is pulled out from the screw hole in the upper support or the lower support and screw coupled again after the upper protruding part or the lower protruding part is moved to a desired position.

In particular, when the patient becomes somewhat accustomed to the use of the snoring prevention device, the patient can easily perform the above correction job at home or in an office without having to visit a dental clinic.

Also, when the patient needs to move the lower jaw bone, for example, to talk or drink water, the snoring prevention device according to the present embodiment can be easily adjusted. For the conventional snoring prevention device, the lower jaw bone can be moved only when the snoring prevention device inserted around the teeth is pulled out from the upper teeth or the lower teeth.

However, according to the present embodiment, the lower jaw bone can be freely moved by moving the lower protruding part caught by the rear side of the upper protruding part in the forward direction and separating the separation prevention portions of the upper protruding part and the lower protruding part, respectively, in the vertical direction to remove the coupling between the upper protruding part and the lower protruding part. That is, the upper protruding part and the lower protruding part can be easily released with a simple movement of the lower jaw bone.

Mode of the Invention

The snoring prevention device 1 according to the present embodiment of the present invention can be modified as described below. In the above-described embodiment, although the upper support 10 and the lower support 30 are arranged between the front teeth and the molars at both sides, the snoring prevention device 1 can be arranged at the front teeth.

Figure 8:
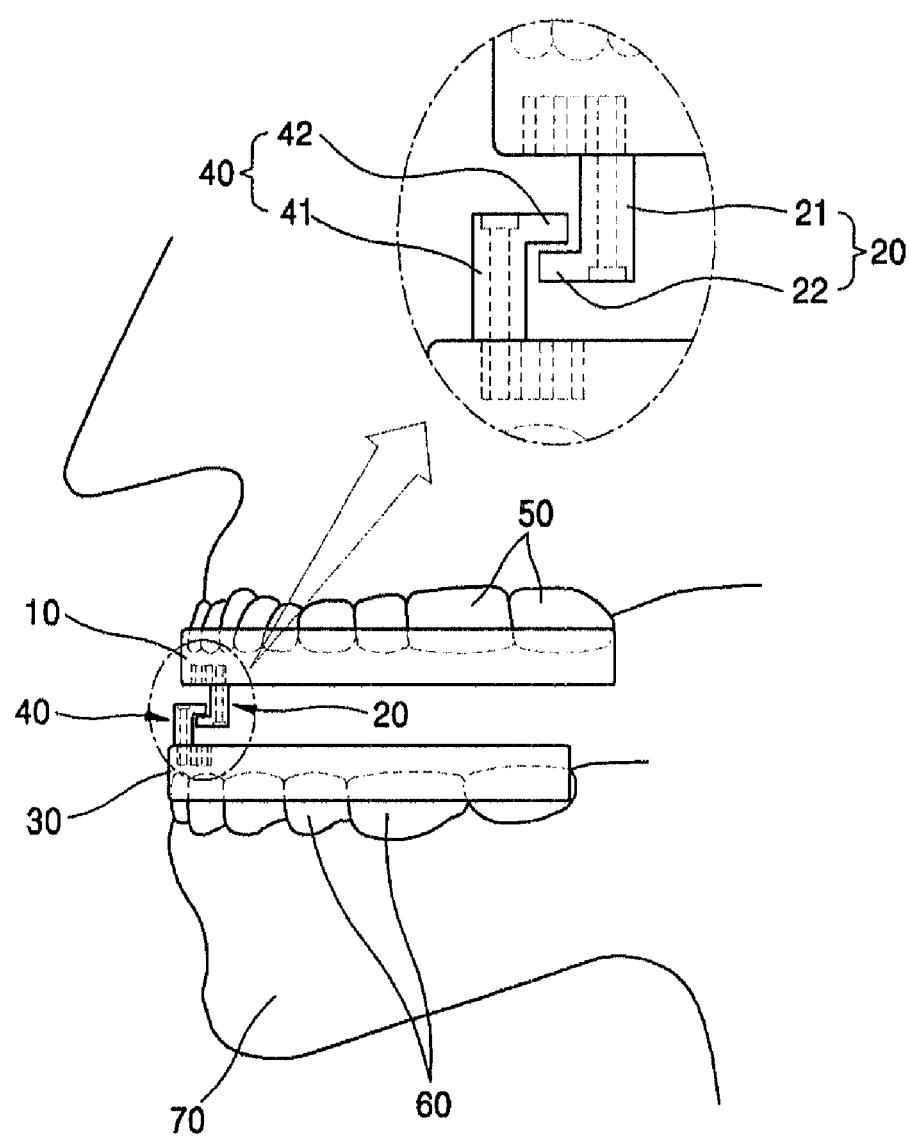
FIG. 8 illustrates that a snoring prevention device according to another embodiment of the present invention is installed between the upper and lower teeth of a patient.
Figure 9:
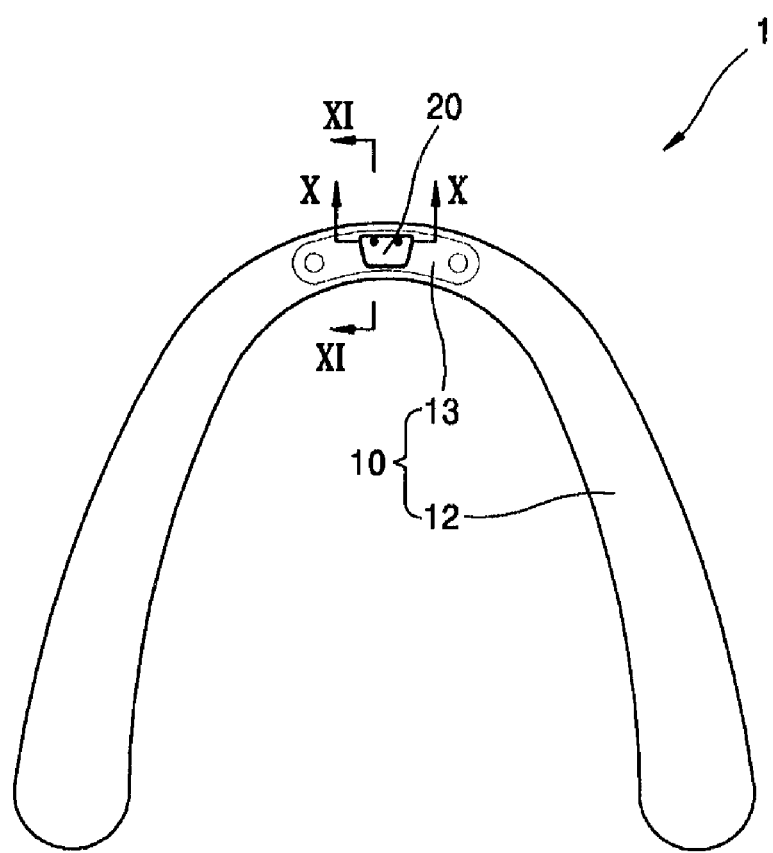
FIG. 9 is a plan view showing an upper support and an upper protruding part of the snoring prevention device of FIG. 8, according to an embodiment of the present invention.
Figure 10:
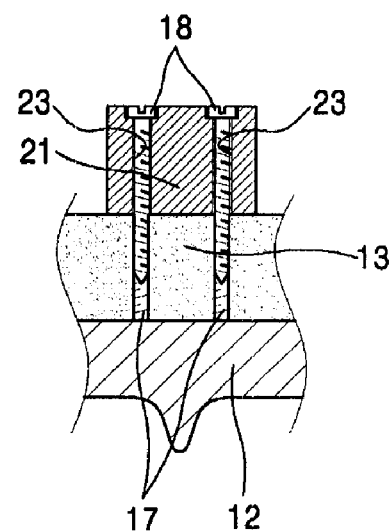
FIG. 10 is a cross-sectional view taken along the line X-X of FIG. 9, according to an embodiment of the present invention.
Figure 11:
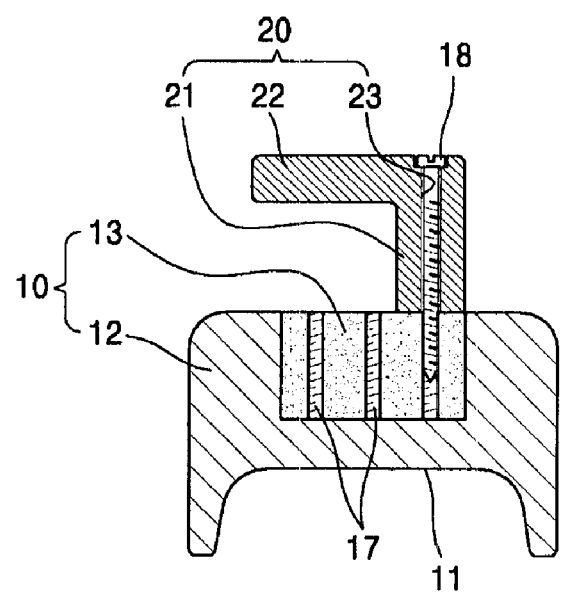
FIG. 11 is a cross-sectional view taken along the line XI-XI of FIG. 9, according to an embodiment of the present invention.

FIG. 8 illustrates that a snoring prevention device according to another embodiment of the present invention is installed between the upper and lower teeth of a patient. FIG. 9 is a plan view showing an upper support and an upper protruding part of the snoring prevention device of FIG. 8, according to an embodiment of the present invention. FIG. 10 is a cross-sectional view taken along the line X-X of FIG. 9, according to an embodiment of the present invention. FIG. 11 is a cross-sectional view taken along the line XI-XI of FIG. 9, according to an embodiment of the present invention.

According to the present embodiment of the present invention, when the upper support 10 is supported by the upper teeth 50 and the lower support 30 is supported by the lower teeth 60, the upper protruding part 20 is located under the front teeth of the upper teeth 50 and the lower protruding part 40 is located above the front teeth of the lower teeth 60. The structures and operations of the upper support 10, the upper protruding part 20, the lower support 30, and the lower protruding part 40 are the same as those of the previously-described embodiment.

In the previously-described embodiment, although the screw hole 17 and the screw member 18 are used as the position adjustment unit 16, a screw member inserted in a long hole formed along the forward and backward direction can be considered, a screw member inserted in a slot formed in the upper support 10 or lower support 30 in the forward and backward direction can be considered. Also, in addition to the screw member, various detachable coupling units can be considered.

Also, in the previously-described embodiment, although each of the upper support 10 and the lower support 30 has the groove portion 11 to cover all the upper teeth 50 or the lower teeth 60, the upper support 10 can be formed of a wire so that the wire is supported on part of the outer surface of the upper teeth 50 or the lower teeth 60 and the upper protruding part 20 or the lower protruding part 40 is fixedly coupled to the wire.

While the present invention has been particularly shown and described with reference to preferred embodiments thereof, it will be understood by those skilled in the art that various changes in form and details may be made therein without departing from the spirit and scope of the invention as defined by the appended claims. The preferred embodiments should be considered in descriptive sense only and not for purposes of limitation. Therefore, the scope of the invention is defined not by the detailed description of the invention but by the appended claims, and all differences within the scope will be construed as being included in the present invention.

The invention claimed is:

1. A snoring prevention device comprising:
an upper support supported by upper teeth of a patient;
an upper protruding part provided at the upper support to protrude downward from the upper support;
a lower support supported by lower teeth of the patient;
a lower protruding part provided at the lower support to protrude upward from the lower support and caught by a front side of the upper protruding part; and
a first position adjustment unit to adjust the position of the upper protruding part with respect to the upper support in a forward/backward direction, wherein the first position adjustment unit comprises:
a plurality of screw holes arranged in the upper support to be separated from each other in the forward/backward direction; and
a screw member selectively coupled to one of the screw holes by penetrating the upper protruding part to allow the upper protruding part to be coupled to the upper support.

2. The device of claim 1, wherein, when the upper support is supported by the upper teeth and the lower support is supported by the lower teeth, the upper protruding part is located under front teeth of the upper teeth and the lower protruding part is located above front teeth of the lower teeth.

3. The device of claim 1, wherein each of the upper protruding part and the lower protruding part is provided in a pair and, when the upper support is supported by the upper teeth and the lower support is supported by the lower teeth, a pair of the upper protruding parts and a pair of the lower protruding parts are symmetrically arranged between front teeth and molars at both sides.

4. The device of claim 1, wherein a groove portion to accommodate at least one of the upper teeth is formed in the upper support and a groove portion to accommodate at least one of the lower teeth is formed in the lower support.

5. The device of claim 4, wherein the groove portion of the upper support is formed to accommodate all upper teeth and the groove portion of the lower support is formed to accommodate all lower teeth.

6. The device of claim 1, wherein the upper protruding part comprises:
a downward extension portion extending downwardly; and
a separation prevention portion extending from a lower end of the downward extension portion to protrude in a forward direction, and
the lower protruding part comprises:
an upward extension portion extending upwardly; and
a separation prevention portion extending from an upper end of the upward extension portion to protrude downwardly and caught by an upper side of the separation prevention portion of the upper protruding part to prevent the upper support and the lower support from being separated from each other.

7. A snoring prevention device comprising:
an upper support supported by upper teeth of a patient;
an upper protruding part provided at the upper support to protrude downward from the upper support;
a lower support supported by lower teeth of the patient;
a lower protruding part provided at the lower support to protrude upward from the lower support and caught by a front side of the upper protruding part; and
a second position adjustment unit to adjust the position of the lower protruding part with respect to the lower support in a forward/backward direction,
wherein the second position adjustment unit comprises:
a plurality of screw holes arranged in the lower support to be separated from each other in the forward/backward direction; and
a screw member selectively coupled to one of the screw holes by penetrating the lower protruding part to allow the lower protruding part to be coupled to the lower support at a desired position of the lower support.

8. The device of claim 7, wherein the upper protruding part comprises:
a downward extension portion extending downwardly; and
a separation prevention portion extending from a lower end of the downward extension portion to protrude in a forward direction, and
the lower protruding part comprises:
an upward extension portion extending upwardly; and
a separation prevention portion extending from an upper end of the upward extension portion to protrude downwardly and caught by an upper side of the separation prevention portion of the upper protruding part to prevent the upper support and the lower support from being separated from each other.

9. The device of claim 7, wherein, when the upper support is supported by the upper teeth and the lower support is supported by the lower teeth, the upper protruding part is located under front teeth of the upper teeth and the lower protruding part is located above front teeth of the lower teeth.

10. The device of claim 7, wherein each of the upper protruding part and the lower protruding part is provided in a pair and, when the upper support is supported by the upper teeth and the lower support is supported by the lower teeth, a pair of the upper protruding parts and a pair of the lower protruding parts are symmetrically arranged between front teeth and molars at both sides.

11. The device of claim 7, wherein a groove portion to accommodate at least one of the upper teeth is formed in the upper support and a groove portion to accommodate at least one of the lower teeth is formed in the lower support.

12. The device of claim 11, wherein the groove portion of the upper support is formed to accommodate all upper teeth and the groove portion of the lower support is formed to accommodate all lower teeth.

13. A snoring prevention device comprising:
an upper support supported by upper teeth of a patient;
an upper protruding part provided at the upper support to protrude downward from the upper support;
a lower support supported by lower teeth of the patient;
a lower protruding part provided at the lower support to protrude upward from the lower support and caught by a front side of the upper protruding part; and
a first position adjustment unit to adjust the position of the upper protruding part with respect to the upper support in a forward/backward direction,
wherein the first position adjustment unit comprises:
a plurality of holes arranged in the upper support to be separated from each other in the forward/backward direction; and
a coupling member selectively coupled to one of the holes by penetrating the upper protruding part to allow the upper protruding part to be coupled to the upper support.

14. A snoring prevention device comprising:
an upper support supported by upper teeth of a patient;
an upper protruding part provided at the upper support to protrude downward from the upper support;
a lower support supported by lower teeth of the patient;
a lower protruding part provided at the lower support to protrude upward from the lower support and caught by a front side of the upper protruding part; and
a second position adjustment unit to adjust the position of the lower protruding part with respect to the lower support in a forward/backward direction,
wherein the second position adjustment unit comprises:
a plurality of holes arranged in the lower support to be separated from each other in the forward/backward direction; and
a coupling member selectively coupled to one of the holes by penetrating the lower protruding part to allow the lower protruding part to be coupled to the lower support at a desired position of the lower support.

* * * * *